United States Patent [19]

Neuzil et al.

[11] 4,049,688

[45] Sept. 20, 1977

[54] PROCESS FOR SEPARATING ESTERS OF FATTY ACIDS BY SELECTIVE ADSORPTION

[75] Inventors: Richard W. Neuzil, Downers Grove; Armand J. deRosset, Clarendon Hills, both of Ill.

[73] Assignee: UOP Inc., Des Plaines, Ill.

[21] Appl. No.: 710,817

[22] Filed: Aug. 2, 1976

[51] Int. Cl.$^2$ .............................................. C11C 1/08
[52] U.S. Cl. .................................. 260/428; 260/428.5
[58] Field of Search ................ 260/420, 428, 666 SA, 260/677 AD, 708, 419, 428.5

[56] References Cited

U.S. PATENT DOCUMENTS

| | | | |
|---|---|---|---|
| 2,696,304 | 12/1954 | Gilmore | 260/666 SA |
| 2,985,589 | 5/1961 | Broughton et al. | 260/676 MS |
| 3,146,277 | 8/1964 | Hawes | 260/677 AD |
| 3,733,261 | 5/1973 | Adams et al. | 260/677 AD |
| 3,969,223 | 7/1976 | Rosback et al. | 260/677 AD |

*Primary Examiner*—Winston A. Douglas
*Assistant Examiner*—John F. Niebling
*Attorney, Agent, or Firm*—James R. Hoatson, Jr.; Thomas K. McBride; William H. Page, II

[57] ABSTRACT

A process for separating an ester of an unsaturated fatty acid from a mixture comprising an ester of an unsaturated fatty acid and an ester of a saturated fatty acid which process comprises contacting the mixture at adsorption conditions with an adsorbent comprising a X or a Y zeolite containing one or more selected cations at the exchangeable cationic sites thereby selectively adsorbing the ester of an unsaturated fatty acid. Preferably the ester of an unsaturated fatty acid will be recovered from the adsorbent by desorption with a desorbent material.

29 Claims, No Drawings

PROCESS FOR SEPARATING ESTERS OF FATTY ACIDS BY SELECTIVE ADSORPTION

BACKGROUND OF THE INVENTION

1. Field of the Invention

The field of art to which this invention pertains is the solid bed adsorptive separation of esters of fatty acids. More specifically the invention relates to a process for separating an ester of an unsaturated fatty acid from an ester of a saturated fatty acid which process employs an adsorbent comprising particular zeolites which selectively adsorbs an ester of an unsaturated fatty acid from a feed mixture containing an ester of an unsaturated fatty acid and an ester of a saturated fatty acid.

2. Description of the Prior Art

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched-chain paraffins and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Y zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; in the process described in U.S. Pat. No. 3,668,267 to separate specific alkyl-substituted naphthalenes. Because of the commercial importance of para-xylene, perhaps the more well-known and extensively used hydrocarbon isomer separation processes are those for separating para-xylene from a mixture of $C_8$ aromatics. In processes described in U.S. Pat. Nos. 3,558,730; 3,558,732; 3,626,020; 3,663,638; and 3,734,974 for example adsorbents comprising particular zeolites are used to separate para-xylene from feed mixtures comprising para-xylene and at least one other xylene isomer by selectively adsorbing para-xylene over the other xylene isomers.

In contrast, our invention relates to the separation of nonhydrocarbons and more specifically to the separation of fatty-acid esters. We have discovered that adsorbents comprising certain zeolites containing one or more selected cations at the exchangeable cationic sites exhibit adsorptive selectivity for an ester of an unsaturated fatty acid with respect to an ester of a saturated fatty acid thereby making separation of such esters by solid-bed selective adsorption possible. In a specific embodiment our process is a process for separating the unsaturated-fatty-acid esters methyl oleate and methyl linoleate from a mixture comprising methyl oleate, methyl linoleate and the saturated-fatty-acid esters methyl palmitate and methyl stearate.

Production of fatty esters is the most important phase in the industrial chemistry of fatty acids. The esters produced are of several types and include those resulting from the reaction of fatty acids with monohydric alcohols, polyhydric alcohols, ethylene or propylene oxide, and acetylene or vinyl acetate. The principal monohydric alcohols are methanol, 1-propanol, 2-propanol and 1-butanol. The greatest uses of esters are in the solvent and plasticizer fields. Esters of monohydric alcohols are used for plasticizers and in cosmetics. Esters of unsaturated fatty acids are used for drying agents.

SUMMARY OF THE INVENTION

It is accordingly a broad objective of our invention to provide a process for separating an ester of an unsaturated fatty acid from a feed mixture containing an ester of an unsaturated fatty acid and an ester of a saturated fatty acid to produce a product stream containing a higher concentration of an ester of an unsaturated fatty acid and a product stream containing a higher concentration of an ester of a saturated fatty acid than were contained in the feed mixture. More specifically it is an objective of our invention to provide a process for separating methyl oleate or methyl linoleate or both from a feed mixture containing methyl oleate or methyl linoleate or both and methyl palmitate or methyl stearate or both.

In brief summary our invention is, in one embodiment, a process for separating an ester of an unsaturated fatty acid from a mixture comprising an ester of an unsaturated fatty acid and an ester of a saturated fatty acid which process comprises contacting at adsorption conditions said mixture with an adsorbent comprising a X or Y zeolite containing at exchangeable cationic sites at least one cation selected from the group consisting of cations of metals of Group IA of the Periodic Table of Elements and combinations thereof thereby selectively adsorbing said ester of an unsaturated fatty acid and thereafter recovering said ester of an unsaturated fatty acid.

In another embodiment our invention is a process for separating an ester of an unsaturated fatty acid from a mixture comprising an ester of an unsaturated fatty acid and an ester of a saturated fatty acid which process comprises the steps of: (a) contacting said mixture at adsorption conditions with an adsorbent comprising a X or a Y zeolite containing at the exchangeable cationic sites at least one cation selected from the group consisting of cations of metals of Group IA of the Periodic Table of Elements and combinations thereof thereby selectively adsorbing said ester of an unsaturated fatty acid; (b) removing from the adsorbent a raffinate stream comprising said ester of a saturated fatty acid; (c) contacting said adsorbent at desorption conditions with a desorbent material comprising a monocyclic aromatic hydrocarbon to effect the desorption of said ester of an unsaturated fatty acid from said adsorbent; and, (d) removing from said adsorbent an extract stream comprising said ester of an unsaturated fatty acid.

In yet another embodiment our invention is a process for separating an ester of an unsaturated fatty acid from a mixture comprising an ester of an unsaturated fatty acid and an ester of a saturated fatty acid which process employs an adsorbent comprising a X or a Y zeolite containing at exchangeable cationic sites at least one cation selected from the group consisting of cations of metals of Group IA of the Periodic Table of Elements and combinations thereof which process comprises the steps of: (a) maintaining net fluid flow through a column of said adsorbent in a single direction, which column contains at least three zones having separate operational functions occurring therein and being serially interconnected with the terminal zones of said column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purification zone immediately upstream from said adsorption zone, said purification zone defined by the adsorbent located between an extract output stream at an upstream boundary of said purification zone and said feed input stream at a downstream boundary of said purification zone; (d) maintaining a desorption zone immediately upstream from said purification zone, said desorption zone defined by the adsorbent located between a desorbent input stream at an upstream boundary of said zone and said extract output stream at a downstream boundary of said zone; (e) passing said feed mixture into said adsorption zone at adsorption conditions to effect the selective adsorption of said ester of an unsaturated fatty acid by said adsorbent in said adsorption zone and withdrawing a raffinate output stream from said adsorption zone; (f) passing a desorbent material comprising a monocyclic aromatic hydrocarbon into said desorption zone at desorption conditions to effect the displacement of said ester of an unsaturated fatty acid from the adsorbent in said desorption zone; (g) withdrawing an extract output stream comprising said ester of an unsaturated fatty acid and desorbent material from said desorption zone; (h) passing at least a portion of said extract output stream to a separation means and therein separating at separation conditions at least a portion of said desorbent material; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

Other objectives and embodiments of our invention encompass details about feed mixtures, adsorbents, desorbent materials and operating conditions all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, an ester of an unsaturated fatty acid is an extract component and an ester of a saturated fatty acid is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components.

The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high-purity, unsaturated-fatty-acid-ester product or a saturated-fatty-acid-ester product (or both) at high recoveries, it will be appreciated that an extract component is never completely adsorbed by the adsorbent, nor is a raffinate component completely non-adsorbed by the adsorbent. Therefore, varying amounts of a raffinate component can appear in the extract stream and, likewise, varying amounts of an extract component can appear in the raffinate stream. The extract and raffinate steams then are further distinguished from each other and from the feed mixture by the ratio of the concentrations of an extract component and a raffinate component appearing in the particular stream. More specifically, the ratio of the concentration of an unsaturated-fatty-acid ester to that of a less selectively adsorbed saturated-fatty-acid ester will be lowest in the raffinate stream, next highest in the feed mixture, and the highest in the extract stream. Likewise, the ratio of the concentration of a less selectively adsorbed saturated-fatty-acid ester to that of a more selectively adsorbed unsaturated-fatty-acid ester will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent passes into an operational zone (hereinafter defined and described) employed in one embodiment of this process its non-selective void volume together with its selective pore volume carries fluid into that zone. The non-selective void volume is utilized in determining the amount of fluid which should pass into the same zone in a counter-current direction to the adsorbent to displace the fluid present in the nonselective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Before considering feed mixtures which can be charged to the process of our invention reference is first made to the production of fatty acids used to make the fatty-acid esters. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched-chain, it is now generally used, and is so used herein, to include also related unsaturated acids, certain substituted acids, and even aliphatic acids containing alicyclic substituents. The naturally occurring fatty acids with a few exceptions are higher straight-chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). As the term "unsaturated fatty acid" is used herein then it shall mean a fatty acid having at least one double bond. Fatty acids are typically prepared from glyceride fats or oils by one of several splitting or hydrolytic processes. In all cases the hydrolysis reaction may be summarized as the reaction of a fat or oil with water to yield fatty acids plus glycerol. In modern fatty acid plants this process is carried out by continuous high-pressure, high-temperature hydrolysis of the fat. Starting materials most commonly used for the production of fatty acids include coconut oil, palm oil, inedible animal fats, fresh oils and the roots of the commonly-used vegetable oils, soybean, cottonseed and corn. The composition of the fatty acids obtained from the splitter is dependent on the fat or oil from which they were made. Rarely will the composition of the fatty acid mixture obtained from the splitter be ideal or even satisfactory for most uses. Hence fractionation is used almost universally to prepare products more desirable for specific end uses than the mixtures obtained from the splitter. Fractionation according to molecular weight is best accomplished in fractional distillation. There is a marked difference in the volatility of any two fatty acids of different chain length, and in practice, the utility of fractional distillation is enhanced by the absence of odd-membered acids in the natural fats, so that 2 carbom atoms is nearly always the minimum difference in chain length of the fatty acids present in a mixture. Fractionating columns in such operation are capable of producing fatty acids of 95% purity or better from the viewpoint of chain length. It is not possible, however, to separate unsaturated fatty acids from each other or from saturated fatty acids by commercial fractional distillation when all have the same chain length. While unsaturated fatty acids can be separated from saturated fatty acids by fractional crystallization with or without the use of solvents, typically a mixture of unsaturated and saturated fatty acids having the same carbon number chain length or having chain lengths over a narrow carbon-number range will be used rather than pure compounds to prepare the end-use products, such as fatty-acid esters. When such a mixture is esterified, such as with a monohydric alcohol, a mixture of unsaturated- and saturated-fatty-acid esters is produced which is equally difficult if not impossible to separate by fractional distillation. Feed mixtures which can be charged to our process then will be those comprising an ester of an unsaturated fatty acid and an ester of a saturated fatty acid. Preferably the esters will each contain from about 8 to about 30 carbon atoms per molecule and will be produced by the reaction of fatty acids with monohydric alcohols. Particularly preferred are methyl and ethyl esters of such fatty acids. The feed mixtures may contain one or more unsaturated-fatty-acid ester, which may be monoethanoid, diethanoid, triethanoid, etc. or mixtures thereof, and one or more saturated-fatty-acid ester. Typically the unsaturated-fatty-acid ester and the saturated-fatty-acid ester will have the same carbon number chain length or will have carbon number chain lengths that do not vary more than about 1 to about 5 carbon numbers from each other. An example of a typical feed mixture is one containing: 1 vol. % $C_{14}$ and lower saturated compounds; 25 vol. % methyl palmitate; 18 vol. % methyl stearate; 44 vol. % methyl oleate; and 11 vol. % methyl linoleate. Except for the small amount of $C_{14}$ material such feed mixture consists of $C_{16}$ and $C_{18}$ methyl esters of fatty acids and more specifically consists of two saturated-fatty-acid esters, one monoethanoid unsaturated-fatty-acid ester and one diethanoid unsaturated-fatty-acid ester. Feed mixtures which can be charged to our process may contain, in addition to fatty-acid esters, a diluent material that is not adsorbed by the adsorbent and which is preferably separable from the extract and raffinate output streams by fractional distillation. Paraffinic hydrocarbons are examples of suitable diluents. Normal heptane is one specific example of a paraffinic hydrocarbon that can be used as a diluent. When a diluent is employed the concentration of diluent in the mixture of diluent and fatty-acid esters will preferably be from a few vol. % up to about 75 vol. % with the remainder being fatty-acid esters.

Desorbent materials used in various prior art adsorptive separation processes vary depending upon such factors as the type of operation employed. In the swing-bed system in which the selectively adsorbed feed component is removed from the adsorbent by a purge stream desorbent selection is not critical and desorbent materials comprising gaseous hydrocarbons such as methane, ethane, etc., or other types of gases such as nitrogen or hydrogen may be used at elevated temperatures or reduced pressures or both to effectively puge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material the purity of the extract product and the raffinate product would not be very high, nor would the desorbent material be available for reuse in the process. It is therefore contemplated than any desorbent material used in this process will preferably have a substantially different average boiling point than that of the feed mixture to allow separation of at least a portion of desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Other separation methods such as reverse osmosis or thin-film evaporation might also be employed alone or in combination with fractional distillation to remove at least a portion of the desorbent material. Finally, desorbent materials should also be materials which are readily available and therefore reasonable in cost. In the preferred isothermal, liquid-phase operation of the process of our invention, we have found that desorbent materials comprising monocyclic aromatic hydrocarbons having average boiling points substantially different from that of a feed mixture meet these requirements and are particularly effective. Preferred monocyclic aromatic hydrocarbons are benzene, toluene, xylenes, ethyl benzene and diethylbenzenes. Usually one of these preferred desorbent materials can be employed with a particular feed mixture such that the requirement of substantially different average boiling points is met. Mixtures of monocyclic aromatics with diluents that are compatible with the adsorbents and feed mixtures used in our process and that are easily separable from the feed mixture are also effective as desorbent materials. Diluents meeting these requirements can be selected from straight-, branched-chain, or cycloparaffins. Typical concentrations of a monocyclic hydrocarbon in such mixtures can be from a few volume percent up to near 100 volume percent of the total desorbent material mixture but such concentrations preferably will be within the range of from about 50 vol. % to about 100 vol. % of the mixture.

The prior art has also recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relatively selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below.

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represents the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of adsorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both all diluted in desorbent is injected for a duration of several minutes. Desorbent flow is resumed, and the tracer and the extract component or the raffinate component (or both) are eluted as in a liquid-solid chromatographic operation. The effluent can be analyzed on-stream or alternatively effluent samples can be collected periodically and later analyzed separately by analytical equipment and traces of the envelopes of corresponding component peaks developed.

From information derived from the test adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous counter-current liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network to form cage-like structures. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves" particularly when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of an unsaturated-fatty-acid ester from saturated-fatty-acid ester is apparently dependent on differences in electrochemical attraction of an unsaturated-fatty-acid ester and the adsorbent and a saturated-fatty-acid ester and the adsorbent rather than on physical size differences in the fatty-acid ester molecules.

In hydrated form, the crystalline aluminosilicates generally encompass those zeolites represented by the Formula 1 below:

Formula 1

$$M_{2/n}O:Al_2O_3:wSiO_2:yH_2O$$

where M is a cation which balances the electrovalence of the aluminum-centered tetrahedra and which is generally referred to as an exchangeable cationic site, $n$ represents the valence of the cation, $w$ represents the moles of $SiO_2$, and $y$ represents the moles of water. The generalized cation M may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,120,007 respectively incorporated herein by reference thereto. The X zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where M represents at least one cation having a valence of not more than 3, $n$ represents the valence of M, and $y$ is a value up to about 9 depending upon the identity of M and the degree of hydration of the crystal. As noted from Formula 2 the $SiO_2/Al_2O_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation M is usually predominately sodium, that is the major cation at the exchangeable cationic sites is sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where M is at least one cation having a valence not more than 3, $n$ represents the valence of M, $w$ is a value greater than about 3 up to about 6, and $y$ is a value up to about 9 depending upon the identity of M and the degree of hydration of the crystal. The $SiO_2/Al_2O_3$ mole ratio for Y zeolites can thus be from about 3 to about 6. Like the X zeolite, the cation M may be one or more of a variety of cations but, as the Y zeolite is initially prepared, the cation M is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well known to those having ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-X or sodium-Y zeolite can be partially or essentially completely replaced with other cations.

The term "base material" as used herein shall refer to a material containing X or Y zeolite and amorphous material which can be used to make the adsorbents used in our process. The zeolite will typically be present in the base material in amounts ranging from about 75 wt. % to about 98 wt. % of the base material based on volatile free composition. Volatile free compositions are generally determined after the base material has been calcined at 900° C. in order to drive off all volatile matter. The remainder of the base material will generally be amorphous material such as silica, alumina or silica-alumina mixtures or compounds, such as clays, which material is present in intimate mixture with the small particles of the zeolite material. This amorphous material may be an adjunct of the manufacturing process for X or Y zeolite (for example, intentionally incomplete purification of either zeolite during its manufacture) or it may be added to relatively pure X or Y zeolite but in either case its usual purpose is as a binder to aid in forming or agglomerating the hard crystalline particles of the zeolite. Normally the base material will be in the form of particles such as extrudates, aggregates, tablets, macrospheres or granules having a desired particle size range. The adsorbent used in our process will preferably have a particle size range of about 16-40 mesh (Standard U.S. Mesh). Examples of suitable base materials which can be used to make the adsorbents employed in our process are Molecular Sieves 13X and SK-40 both of which are available from the Linde Company, Tonawanda, New York. The first material of course contains X zeolite while the latter material contains Y zeolite.

We have found that X or Y zeolites containing certain cations at the exchangeable cationic sites possess the selectivity requirement and other necessary requirements previously discussed and are therefore suitable for use in the process. Specifically we have found that adsorbents comprising a X or a Y zeolite containing at exchangeable cationic sites at least one cation selected from the group consisting of cations of metals of Group IA of the Periodic Table of Elements are suitable for use in our process. Preferably the adsorbent for use in our process will comprise a X or a Y zeolite containing sodium or potassium cations at the exchangeable cationic sites. Because of its higher selectivities for an unsaturated-fatty-acid ester with respect to a saturated-fatty-acid ester, an adsorbent comprising a X or a Y zeolite containing potassium cations at the exchangeable cationic sites is more preferred than one containing sodium cations at the exchangeable cationic sites. Preferably the X or Y zeolite will be essentially completely exchanged with the selected cation or cations. A non-sodium X or Y zeolite is deemed to be essentially completely exchanged when the residual sodium content of the zeolite after ion exchange is less than about 2 wt. % $Na_2O$. A sodium-X or sodium-Y zeolite is deemed to be essentially completely exchanged when the amount of non-sodium cations occupying exchangeable cationic sites is less than about 2 wt. %.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of our process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid zone in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone of zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Reference can be made to D. B. Broughton U.S. Pat. No. 2,985,589, and to a paper entitled "Continuous Adsorptive Processing — A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° C. with about 20° C. to about 100° C. being more preferred and a pressure range of from about atmospheric to about 500 psig. with from about atmospheric to about 250 psig. being more preferred to insure liquid phase. Desorption conditions will include the same range of temperatures and pressures as used for adsorption conditions.

The size of the units which can utilize the process of this invention can vary anywhere from those of pilot-plant scale (see for example our assignee's U.S. Pat. No. 3,706,812) to those of commercial scale and can range in flow rates from as little as a few cc. an hour up to many thousands of gallons per hour.

The following examples are presented to illustrate the selectivity relationship that mades the process of our invention possible and are not intended to unduly restrict the scope and spirit of the claims attached hereto.

EXAMPLE I

This example presents selectivities on a desorbent-free basis for an unsaturated-fatty-acid ester with respect to a saturated-fatty-acid ester which were obtained by conducting preliminary pulse tests with a Na-X adsorbent and a K-X adsorbent. The adsorbents were produced by essentially completely exchanging two portions of Linde 13X Molecular Sieves with Na and K cations. Both adsorbents had a particle size range of approximately 20–40 U.S. Mesh. The ester feed mixture was a mixture of methyl esters of fatty acids having the composition shown in Table 1:

Table No. 1

| Feed Mixture Composition, Vol.% Methyl Esters of Fatty Acids | |
|---|---|
| $C_{14}$ and lower saturated | 1 |
| $C_{16}$ saturated (methyl palmitate) | 25 |
| $C_{18}$ saturated (methyl stearate) | 18 |
| $C_{18}^=$ one double bond (methyl oleate) | 45 |
| $C_{18}^{\overline{=}}$ two double bonds (methyl linoleate) | 11 |
| | 100 |

The general pulse-test apparatus and procedure have been previously described. The adsorbents were tested in a 70 cc coiled column maintained at a temperature of 125° C. and a pressure of 50 psig. The 70 cc column of adsorbent was first loaded to equilibrium with a 25 vol. % blend of the above method esters in normal heptane by passing the blend through the column at a nominal liquid hourly space velocity (LHSV) of about 1.0 until the composition of the effluent as determined by G.L.C. analysis was the same as that of the feed blend. Because of the long retention times of the isomers from the G.L.C. analysis the effluent was collected in the automatic sample collector and each fraction, taken over a period of about 2½ minutes, was analyzed later. Normal heptane alone was then passed through the column at about the same LHSV to flush out the interstitial voids in the adsorbent. The methyl esters were then desorbed from the adsorbent by passing toluene as the desorbent material through the column at a LHSV of about 1.0. The concentration of the various esters in automatically-collected effluent samples were determined by G.L.C. analysis and from these concentrations the selectivities of each adsorbent from the unsaturated-fatty-acid esters with respect to the saturated-fatty-acid esters in the absence of desorbent material were calculated and are given below in Table 2:

Table No. 2

SELECTIVITIES OF Na-X AND K-X ZEOLITE ADSORBENTS FOR UNSATURATED OVER SATURATED METHYL ESTERS OF FATTY ACIDS (Desorbent Free Basis)

| Adsorbent | Na-X | K-X |
|---|---|---|
| Selectivities for: | | |
| $C_{18}^=/C_{16}$ | 1.2 | 2.1 |
| $C_{18}^=/C_{18}$ | 1.9 | 4.0 |
| $C_{18}^{\overline{=}}/C_{16}$ | 1.7 | 6.7 |
| $C_{18}^{\overline{=}}/C_{18}$ | 2.5 | 14.5 |

With selectivities of 2.0 or greater, it is apparent that the K-X adsorbent is preferred over the Na-X adsorbent.

EXAMPLE II

This example presents selectivities, obtained in the presence of various desorbent materials, of a K-X and a K-Y adsorbent from an unsaturated-fatty-acid ester with respect to a saturated-fatty-acid ester. Five tests were run, two with a K-X zeolite adsorbent and three with a K-Y zeolite adsorbent. Four desorbent materials were used — toluene, para-diethylbenzene, m-xylene and benzene. The K-X adsorbent was the same as was used in Example I and the K-Y adsorbent was prepared by essentially completely exchanging a portion of Linde SK-40 with K cations. Both adsorbents had a particle size range of approximately 20–40 U.S. Mesh. The ester feed mixture was the same as that described in Example I as was the test operating pressure. Operating temperatures of 125° C. and 160° C. were used. The sequence of operations for each test was as follows. A desorbent material was continuously run through the column containing the adsorbent at a nominal liquid hourly space velocity (LHSV) of about 1.0. At a convenient time the flow of desorbent material was stopped, and a 10 cc sample composed of 25 vol. % of the methyl ester feed mixture, 5 vol. % cetane (used as a tracer material to establish the nonselective void volume of the adsorbent) and 70 vol. % of a desorbent material was injected into the column via a sample loop and the flow of desorbent material was resumed. Samples of the effluent were automatically collected in an automatic sample collector and later analyzed by G.L.C. analysis. From the analysis of these samples peak envelope concentrations were developed for the methyl esters and the cetane traces. The retention volume for the methyl esters were calculated by measuring the distances from time zero on the reference point to the respective midpoints of the methyl esters and subtracting the distance representing the void volume of the adsorbent obtained by measuring the distance from the same reference point to the midpoint of the cetane peak. The selectivities of an adsorbent for an ester of an unsaturated fatty acid with respect to an ester of a saturated fatty acid in the presence of a desorbent material are in the quotients obtained by dividing the retention volume for an unsaturated-fatty-acid ester by the retention volume for a saturated-fatty-acid ester. The results for these pulse tests are shown in Table No. 3 below.

Table No. 3

SELECTIVITIES OF K-X ZEOLITE ADSORBENTS FOR UNSATURATED OVER SATURATED METHYL ESTERS OF FATTY ACIDS WITH VARIOUS DESORBENTS

| Test | 1 | 2 | 3 | 4 | 5 |
|---|---|---|---|---|---|
| Adsorbent | K-X | K-X | K-Y | K-Y | K-Y |
| Desorbent | Toluene | P-DEB | m-Xylene | Toluene | Benzene |
| Process Temp., ° C. | 125 | 125 | 160 | 160 | 160 |
| Retention Vols., cc | | | | | |
| $C_{16}$ | 1.5 | 2.5 | 7.0 | 2.7 | 2.2 |
| $C_{18}$ | 0.75 | 1.2 | 3.1 | 2.0 | 1.8 |
| $C_{18}^=$ | 2.25 | 4.2 | 9.0 | 4.2 | 2.50 |
| $C_{18}^=$ | 8.5 | 17.6 | 45.5 | 12.5 | 5.47 |
| Selectivities: | | | | | |
| $C_{18}^=/C_{16}$ | 1.5 | 1.7 | 1.3 | 1.5 | 1.1 |
| $C_{18}^=/C_{18}$ | 3.0 | 3.5 | 2.9 | 2.1 | 1.4 |
| $C_{18}^=/C_{16}$ | 5.6 | 7.0 | 6.5 | 4.0 | 2.4 |
| $C_{18}^=/C_{18}$ | 11.3 | 14.7 | 15.0 | 6.1 | 3.1 |

Since selectivities for all five tests for an unsaturated-fatty-acid ester with respect to a saturated-fatty-acid ester were greater than 1.0, these pulse tests illustrate the ability of the adsorbents to preferentially adsorb, in the presence of the various desorbent materials, an unsaturated-fatty-acid ester over a saturated-fatty-acid ester thereby making our process possible. As the test data shows the highest selectivities were for Test 2, obtained with a K-X zeolite adsorbent, para-diethylbenzene desorbent material and a process temperature of 125° C. and the lowest selectivities were for Test 5 which used a K-Y zeolite absorbent, benzene desorbent material and a process temperature of 160° C. A comparison of Test 1 and Test 2 selectivities indicates that para-diethylbenzene is a better desorbent material than is toluene when used with a K-X zeolite adsorbent and a 125° C. process temperature and a comparison of selectivities for Tests 3, 4 and 5 indicates that m-xylene and toluene are better desorbent materials than is benzene when used with a K-Y zeolite adsorbent and a process temperature of 160° C.

We claim as our invention:

1. A process for separating an ester of an unsaturated fatty acid from a mixture comprising an ester of an unsaturated fatty acid and an ester of a saturated fatty acid which process comprises contacting at a temperature within the range of from about 20° C. to about 200° C. and a pressure within the range from about atmospheric to about 500 psig. said mixture with an adsorbent comprising a X or Y zeolite containing at exchangeable cationic sites at least one cation selected from the group consisting of cations of metals of Group IA of the Periodic Table of Elements and combinations thereof thereby selectively adsorbing said ester of an unsaturated fatty acid and thereafter recovering said ester of an unsaturated fatty acid.

2. The process of claim 1 further characterized in that said adsorbent contains sodium cations at the exchangeable cationic sites.

3. The process of claim 1 further characterized in that said adsorbent contains potassium cations at the exchangeable cationic sites.

4. The process of claim 1 further characterized in that it is effected in the liquid phase.

5. The process of claim 1 further characterized in that said ester of an unsaturated fatty acid and said ester of a saturated fatty acid each contain from about 8 to about 30 carbon atoms per molecule.

6. The process of claim 5 further characterized in that said ester of an unsaturated fatty acid and said ester of a saturated fatty acid are methyl esters.

7. The process of claim 6 further characterized in that said ester of a saturated fatty acid is methyl palmitate or methyl stearate.

8. The process of claim 6 further characterized in that said ester of an unsaturated fatty acid is methyl oleate.

9. The process of claim 6 further characterized in that said ester of an unsaturated fatty acid is methyl linoleate.

10. The process of claim 1 further characterized in that said ester of an unsaturated fatty acid is recovered by desorption with a desorbent material comprising a monocyclic aromatic hydrocarbon.

11. A process for separating an ester of an unsaturated fatty acid from a mixture comprising an unsaturated fatty acid and an ester of a saturated fatty acid which process comprises the steps of:

a. contacting said mixture at a temperature within the range of from about 20° C. to about 200° C. and a pressure from about atmospheric pressure to about 500 psig. with an adsorbent comprising a X or a Y zeolite containing at the exchangeable cationic sites at least one cation selected from the group consisting of cations of metals of Group IA of the Periodic Table of Elements and combinations thereof thereby selectively adsorbing said ester of an unsaturated fatty acid;

b. removing from the adsorbent a raffinate stream comprising said ester of a saturated fatty acid;

c. contacting said adsorbent at a temperature within the range of from about 20° C. to about 200° C. and a pressure from about atmospheric pressure to about 500 psig. with a desorbent material comprising a monocyclic aromatic hydrocarbon to effect the desorption of said ester of an unsaturated fatty acid from said adsorbent; and, d. removing from said adsorbent an extract stream comprising said ester of an unsaturated fatty acid.

12. The process of claim 11 further characterized in that said adsorbent contains sodium cations at the exchangeable cationic sites.

13. The process of claim 11 further characterized in that said adsorbent contains potassium cations at the exchangeable cationic sites.

14. The process of claim 11 further characterized in that said ester of an unsaturated fatty acid and said ester of a saturated fatty acid each contain from about 8 to about 30 carbon atoms per molecule.

15. The process of claim 14 further characterized in that said ester of an unsaturated fatty acid and said ester of a saturated fatty acid are methyl esters.

16. The process of claim 15 further characterized in that said ester of a saturated fatty acid is methyl palmitate or methyl stearate.

17. The process of claim 15 further characterized in that said ester of an unsaturated fatty acid is methyl oleate.

18. The process of claim 15 further characterized in that said ester of an unsaturated fatty acid is methyl linoleate.

19. The process of claim 11 further characterized in that said monocyclic aromatic hydrocarbon is selected from the group consisting of benzene, toluene, xylenes, ethylbenzene and diethylbenzenes.

20. A process for separating an ester of an unsaturated fatty acid from a mixture comprising an ester of an unsaturated fatty acid and an ester of a saturated fatty acid which process employs an adsorbent comprising a X or a Y zeolite containing at exchangeable cationic sites at least one cation selected from the group consisting of cations of metals of Group IA of the Periodic Table of Elements and combinations thereof which process comprises the steps of:

a. maintaining net fluid flow through a column of said absorbent in a single direction, which column contains at least three zones having separate operational functions occurring therein and being serially interconnected with the terminal zones of said column connected to provide a continuous connection of said zones;

b. maintaining an adsorption zone in said column, said zone defined by the adsorbent located between a feed input stream at an upstream boundary of said zone and a raffinate output stream at a downstream boundary of said zone;

c. maintaining a purification zone immediately upstream from said adsorption zone, said purification zone defined by the adsorbent located between an extract output stream at an upstream boundary of said purification zone and said feed input stream at a downstream boundary of said purification zone;

d. maintaining a desorption zone immediately upstream from said purification zone, said desorption zone defined by the adsorbent located between a desorbent input stream at an upstream boundary of said zone and said extract output stream at a downstream boundary of said zone;

e. passing said feed mixture into said adsorption zone at a temperature within the range of from about 20° C. to about 200° C. and a pressure within the range of from about atmospheric to about 500 psig. to effect the selective adsorption of said ester of an unsaturated fatty acid by said adsorbent in said adsorption zone and withdrawing a raffinate output stream from said adsorption zone;

f. passing a desorbent material comprising a monocyclic aromatic hydrocarbon into said desorption zone at a temperature within the range of from about 20° C. to about 200° C. and a pressure within the range of from about atmospheric to about 500 psig. to effect the displacement of said ester of an unsaturated fatty acid from the adsorbent in said desorption zone;

g. withdrawing an extract output stream comprising said ester of an unsaturated fatty acid and desorbent material from said desorption zone;

h. passing at least a portion of said extract output stream to a separation means and therein separating at separation conditions at least a portion of said desorbent material; and, i. periodically advancing through said column of adsorbent in a downstream direction with respect to fluid flow in said adsorption zone the feed input stream, raffinate output stream desorbent input stream and extract output stream to effect the shifting of zones through said adsorbent and the production of extract output and raffinate output streams.

21. The process of claim 20 further characterized in that it includes the step of passing at least a portion of said raffinate output stream to a separation means and therein separating at separation conditions at least a portion of said desorbent material to produce a raffinate product having a reduced concentration of desorbent material.

22. The process of claim 20 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

23. The process of claim 20 further characterized in that said adsorbent contains sodium cations at the exchangeable cationic sites.

24. The process of claim 20 further characterized in that said adsorbent contains potassium cations at the exchangeable cationic sites.

25. The process of claim 20 further characterized in that said ester of an unsaturated fatty acid and said ester of a saturated fatty acid each contain from about 8 to about 30 carbon atoms per molecule.

26. The process of claim 25 further characterized in that said ester of an unsaturated fatty acid and said ester of a saturated fatty acid are methyl esters.

27. The process of claim 26 further characterized in that said ester of a saturated fatty acid is methyl palmitate or methyl stearate.

28. The process of claim 26 further characterized in that said ester of an unsaturated fatty acid is methyl oleate.

29. The process of claim 26 further characterized in that said ester of an unsaturated fatty acid is methyl linoleate.

* * * * *